US012044342B2

(12) United States Patent
Hartridge et al.

(10) Patent No.: US 12,044,342 B2
(45) Date of Patent: Jul. 23, 2024

(54) FLUID CONNECTOR WITH SLIDABLE MEMBER

(71) Applicant: CYTIVA US LLC, Marlborough, MA (US)

(72) Inventors: Thomas James Hartridge, Portsmouth (GB); Davi Uliana, Portsmouth (GB); Daniel J. Kesselaar, Portsmouth (GB)

(73) Assignee: CYTIVA US LLC, Marlborough, MA (US)

( * ) Notice: Subject to any disclaimer, the term of this patent is extended or adjusted under 35 U.S.C. 154(b) by 167 days.

(21) Appl. No.: 17/563,842

(22) Filed: Dec. 28, 2021

(65) Prior Publication Data

US 2023/0204137 A1    Jun. 29, 2023

(51) Int. Cl.
*F16L 37/00* (2006.01)
*A61M 39/10* (2006.01)
(Continued)

(52) U.S. Cl.
CPC ........... *F16L 37/008* (2013.01); *A61M 39/10* (2013.01); *F16K 11/20* (2013.01); *F16L 37/101* (2013.01);
(Continued)

(58) Field of Classification Search
CPC ........ F16K 11/20; F16K 11/22; F16K 11/207; F16K 27/003; A61M 2039/224;
(Continued)

(56) References Cited

U.S. PATENT DOCUMENTS

| | | | | |
|---|---|---|---|---|
| 4,340,203 A | * | 7/1982 | Donner | F16K 24/02 137/625.68 |
| 4,423,741 A | * | 1/1984 | Levy | A61B 10/007 137/625.68 |

(Continued)

FOREIGN PATENT DOCUMENTS

| | | |
|---|---|---|
| CN | 201568609 U | 9/2010 |
| CN | 107709866 A | 2/2018 |

(Continued)

OTHER PUBLICATIONS

Japanese Patent Office, Office Action issued in counterpart Japanese Patent Application No. 2022-181744, mailed on Nov. 14, 2023.

(Continued)

*Primary Examiner* — Zachary T Dragicevich
*Assistant Examiner* — Alexander T Rufrano
(74) *Attorney, Agent, or Firm* — Leydig, Voit & Mayer, Ltd.

(57) ABSTRACT

A connector is provided comprising a first hollow connector body having an inner face including a slot, and an outer face, the first hollow connector body having an aperture passing through the inner face and the outer face; a second hollow connector body having an inner face including a slot, and an outer face, the second hollow connector body having an aperture passing through the inner face and the outer face; and, a fluid transfer member, interposed between the first hollow connector body and the second hollow connector body, wherein the fluid transfer member is slidably arranged in the slot of the inner face of the first hollow body and the slot of the inner face of the second hollow body to provide slidable movement between a first fluid transfer position and a second fluid transfer position.

8 Claims, 21 Drawing Sheets

(51) Int. Cl.
  *A61M 39/22* (2006.01)
  *F16K 11/20* (2006.01)
  *F16L 37/10* (2006.01)
  *F16L 37/46* (2006.01)

(52) U.S. Cl.
  CPC .......... *F16L 37/46* (2013.01); *A61M 39/223* (2013.01); *A61M 2039/224* (2013.01); *F16L 2201/44* (2013.01)

(58) Field of Classification Search
  CPC .............. A61M 39/223; A61M 39/18; A61M 39/1011; A61M 39/1055; F16L 37/38; F16L 37/46; F16L 2201/44; F16L 27/093
  See application file for complete search history.

(56) References Cited

U.S. PATENT DOCUMENTS

| | | | |
|---|---|---|---|
| 4,456,026 A | 6/1984 | Kantor | |
| 4,819,684 A | 4/1989 | Zaugg et al. | |
| 6,679,529 B2 | 1/2004 | Johnson et al. | |
| 7,488,446 B2 | 5/2009 | Meyer et al. | |
| 7,546,857 B2 | 6/2009 | Chadbourne et al. | |
| 7,631,660 B2 | 12/2009 | deCler et al. | |
| 9,726,308 B2 | 8/2017 | Williams et al. | |
| 10,234,042 B2 | 3/2019 | Bowdery | |
| 10,247,342 B2 | 4/2019 | Kesselaar | |
| 10,946,183 B2 | 3/2021 | Faldt et al. | |
| 11,116,957 B2 | 9/2021 | Ueda et al. | |
| 11,571,540 B2* | 2/2023 | Weikert | A61M 16/20 |
| 2002/0000253 A1* | 1/2002 | Fillmore | A61F 5/4405 |
| | | | 137/607 |
| 2007/0102450 A1 | 5/2007 | Stiers | |
| 2009/0198209 A1 | 8/2009 | Usher et al. | |
| 2009/0204078 A1* | 8/2009 | Mitchell | A61M 39/223 |
| | | | 604/246 |
| 2014/0124087 A1 | 5/2014 | Anderson et al. | |
| 2017/0284584 A1 | 10/2017 | Kesselaar et al. | |
| 2017/0299099 A1 | 10/2017 | Williams et al. | |
| 2017/0368325 A1 | 12/2017 | Ueda | |
| 2018/0296817 A1 | 10/2018 | Burdge | |
| 2019/0298985 A1 | 10/2019 | Truong et al. | |
| 2019/0368630 A1 | 12/2019 | Fortner et al. | |
| 2020/0025310 A1 | 1/2020 | McLaughlin et al. | |
| 2020/0032922 A1 | 1/2020 | Wilhelm | |
| 2020/0171234 A1 | 6/2020 | Cowan et al. | |
| 2020/0386330 A1 | 12/2020 | Stanton et al. | |

FOREIGN PATENT DOCUMENTS

| | | |
|---|---|---|
| CN | 108030976 A | 5/2018 |
| EP | 0 639 389 A1 | 2/1995 |
| EP | 3 488 895 A1 | 5/2019 |
| EP | 3 225 895 B1 | 10/2019 |
| JP | S62-243563 A | 10/1987 |
| WO | WO 2009/097321 A1 | 8/2009 |

OTHER PUBLICATIONS

IPOS, Search Report issued in Singaporean Patent Application No. 10202260042P, dated on May 25, 2023.

European Patent Office, Extended European Search Report issued in European Patent Application No. 22207300.9, mailed on May 10, 2023.

* cited by examiner

FLUID CONNECTOR WITH SLIDABLE MEMBER

BACKGROUND OF THE INVENTION

Connectors for use in fluid processing systems and fluid processing (such as liquid products used in the pharmaceutical and biotechnological industries) are known. However, there is a need for improved connectors. The present invention provides for ameliorating at least some of the disadvantages of the prior art. These and other advantages of the present invention will be apparent from the description as set forth below.

BRIEF SUMMARY OF THE INVENTION

An aspect of the invention provides a connector, comprising (a) a first hollow connector body having an inner face including a slot, and an outer face, the first hollow connector body having an aperture passing through the inner face and the outer face; (b) a second hollow connector body having an inner face including a slot, and an outer face, the second hollow connector body having an aperture passing through the inner face and the outer face; and, (c) a fluid transfer member, interposed between the first hollow connector body and the second hollow connector body, wherein the fluid transfer member is slidably arranged in the slot of the inner face of the first hollow body and the slot of the inner face of the second hollow body to provide slidable movement between a first fluid transfer position and a second fluid transfer position, the fluid transfer member having a first surface facing the slot of the inner face of the first hollow body and a second surface facing the slot of the inner face of the second hollow body, and having a first fluid transfer aperture passing through the first surface, and a second fluid transfer aperture passing through the first surface and the second surface; the fluid transfer member having a first open end and a second closed end, wherein the first open end is in fluid communication with the first fluid transfer aperture, without fluid communication with the second fluid transfer aperture, providing a first fluid flow path through the first open end and the first fluid transfer aperture when the fluid transfer member is in the first fluid transfer position; and providing a second fluid flow path through the aperture of the first hollow connector body, the second fluid transfer aperture of the fluid transfer member, and the aperture of the second hollow connector body when the fluid transfer member is in the second fluid transfer position.

In a preferred aspect of the connector, the outer face of the first hollow connector body includes an integrally formed locking mechanism; the integrally formed locking mechanism comprising at least one lug including a slot, and at least one ramp; and an anti-actuation assembly engagement portion comprising at least one recess and/or at least one protrusion; and, the outer face of the second hollow connector body includes an integrally formed locking mechanism; the integrally formed locking mechanism comprising at least one lug including a slot, and at least one ramp; and an anti-actuation assembly engagement portion comprising at least one recess and/or at least one protrusion.

In another aspect, a connector assembly is provided, comprising an aspect of the connector, further comprising a first removable cap, engaged with the first hollow connector body, wherein the removable anti-actuation assembly is interposed between the first removable cap and the first hollow connector body, the first removable cap covering the outer face of the first hollow connector body; and, a second removable cap, engaged with the second hollow connector body, wherein the removable anti-actuation assembly is interposed between the second removable cap and the second hollow connector body, the second removable cap covering the outer face of the second hollow connector body.

In accordance with yet other aspects of the invention, a method for making fluid connections and a method for processing fluid are provided.

BRIEF DESCRIPTION OF THE SEVERAL VIEWS OF THE DRAWING(S)

FIG. 1A is a drawing showing a cross-sectional view of a first connector in a first fluid transfer position according to an aspect of the invention (also showing anti-actuation subassemblies and peel strips connected to outer faces of first and second hollow connector bodies), wherein a fluid transfer member is slidably arranged between a first hollow connector body and a second hollow connector body; FIG. 1B is a drawing showing a cross-sectional view of the first connector shown in FIG. 1A in a second fluid transfer position according to an aspect of the invention (with anti-actuation subassemblies and peel strips removed); FIG. 1C is a drawing showing a cross-sectional view of first and second connectors according to an aspect of the invention joined, wherein the first connector is in the second fluid transfer position as shown in FIG. 1B, and the second connector is in the first fluid transfer position (the second connector having an anti-actuation subassembly and a peel strip).

FIG. 2A is a drawing showing a side perspective view of the first connector shown in FIG. 1A; FIG. 2B is a drawing showing a side view of the first connector shown in FIG. 1B; FIG. 2C is a drawing showing a rear perspective view of the joined first and second connectors shown in FIG. 1C; and 2D is a drawing showing a front view of the joined first and second connectors shown in FIG. 2C.

FIG. 3A is a drawing showing a rear perspective view of the first connector shown in FIG. 2A, showing a hollow connector outer body face with the anti-actuation subassemblies and peel strips removed from each outer body face. FIG. 3B is a drawing showing a perspective view of the anti-actuation subassembly of the anti-actuation assembly comprising a tab and a peelable strip in the connector arrangable between connectors, also showing another subassembly of the anti-actuation assembly used when first and second connector are connected.

FIG. 4A is a drawing showing a cross-sectional view of the fluid transfer member shown in FIG. 1A; FIG. 4B is a drawing showing a top view of the fluid transfer member; FIG. 4C is a drawing showing a bottom view of the fluid transfer member; FIG. 4D is a drawing showing a bottom perspective view of the fluid transfer member shown in FIG. 4C; FIG. 4E is a drawing showing an end view showing the first open end of the fluid transfer member, and FIG. 4F is a drawing showing an end view showing the second closed end of the fluid transfer member.

FIG. 5A is a drawing showing a perspective view of an inner face of a hollow connector body of the first connector also showing an anti-actuation subassembly and peel strip connected to the outer face of the hollow connector body; FIG. 5B is a drawing showing a top view the inner face of a hollow connector body of the first connector shown in FIG. 5A; and FIG. 5C is a drawing s showing a perspective top view of an outer face of the hollow connector body of the first connector shown in FIG. 5A.

DETAILED DESCRIPTION OF THE INVENTION

Figure 1A:
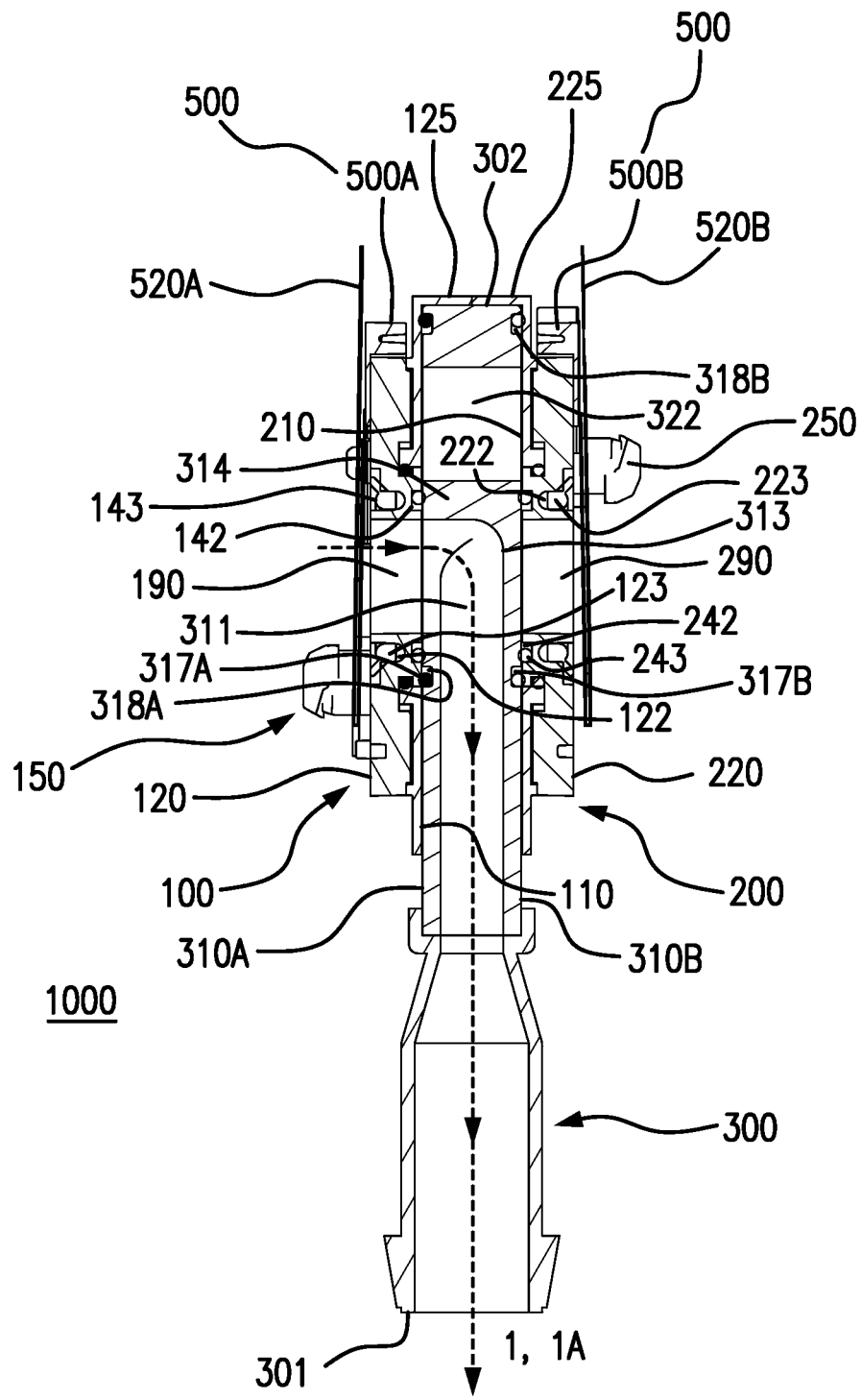

In accordance with an aspect of the invention, a connector is provided, comprising (a) a first hollow connector body having an inner face including a slot, and an outer face, the first hollow connector body having an aperture passing through the inner face and the outer face; (b) a second hollow connector body having an inner face including a slot, and an outer face, the second hollow connector body having an aperture passing through the inner face and the outer face; and, (c) a fluid transfer member, interposed between the first hollow connector body and the second hollow connector body, wherein the fluid transfer member is slidably arranged in the slot of the inner face of the first hollow body and the slot of the inner face of the second hollow body to provide slidable movement between a first fluid transfer position and a second fluid transfer position, the fluid transfer member having a first surface facing the slot of the inner face of the first hollow body and a second surface facing the slot of the inner face of the second hollow body, and having a first fluid transfer aperture passing through the first surface, and a second fluid transfer aperture passing through the first surface and the second surface; the fluid transfer member having a first open end and a second closed end, wherein the first open end is in fluid communication with the first fluid transfer aperture, without fluid communication with the second fluid transfer aperture, providing a first fluid flow path through the first open end and the first fluid transfer aperture when the fluid transfer member is in the first fluid transfer position; and providing a second fluid flow path through the aperture of the first hollow connector body, the second fluid transfer aperture of the fluid transfer member, and the aperture of the second hollow connector body when the fluid transfer member is in the second fluid transfer position.

In a preferred aspect of the connector, the outer face of the first hollow connector body includes a first annular groove with a first resilient deformable annular seal arranged in the first annular groove around the aperture; and the outer face of the second hollow connector body includes a second annular groove with a second resilient deformable annular seal arranged in the second groove around the aperture.

In some aspects of the connectors, the first resilient annular seal in the first annular groove and the second resilient annular seal in the second annular groove each have a lip surrounding the central aperture.

In a preferred aspect of the connector, the outer face of the first hollow connector body includes an integrally formed locking mechanism; the integrally formed locking mechanism comprising at least one lug including a slot, and at least one ramp; and an anti-actuation assembly engagement portion comprising at least one recess and/or at least one protrusion; and, the outer face of the second hollow connector body includes an integrally formed locking mechanism; the integrally formed locking mechanism comprising at least one lug including a slot, and at least one ramp; and an anti-actuation assembly engagement portion comprising at least one recess and/or at least one protrusion.

In another aspect, a connector assembly is provided, comprising an aspect of the connector, further comprising a first removable cap, engaged with the first hollow connector body, wherein the removable anti-actuation assembly is interposed between the first removable cap and the first hollow connector body, the first removable cap covering the outer face of the first hollow connector body; and, a second removable cap, engaged with the second hollow connector body, wherein the removable anti-actuation assembly is interposed between the second removable cap and the second hollow connector body, the second removable cap covering the outer face of the second hollow connector body.

In accordance with yet another aspect of the invention, a method for making fluid connections is provided, the method comprising (A) placing a first connector comprising (a) a first hollow connector body having an inner face including a slot, and an outer face, the first hollow connector body having an aperture passing through the inner face and the outer face; (b) a second hollow connector body having an inner face including a slot, and an outer face, the second hollow connector body having an aperture passing through the inner face and the outer face; and, (c) a fluid transfer member, interposed between the first hollow connector body and the second hollow connector body, wherein the fluid transfer member is slidably arranged in the slot of the inner face of the first hollow body and the slot of the inner face of the second hollow body to provide slidable movement between a first fluid transfer position and a second fluid transfer position, the fluid transfer member having a first surface facing the slot of the inner face of the first hollow body and a second surface facing the slot of the inner face of the second hollow body, and having a first fluid transfer aperture passing through the first surface, and a second fluid transfer aperture passing through the first surface and the second surface; the fluid transfer member having a first open end and a second closed end, wherein the first open end is in fluid communication with the first fluid transfer aperture, without fluid communication with the second fluid transfer aperture, providing a first fluid flow path through the first open end and the first fluid transfer aperture when the fluid transfer member is in the first fluid transfer position; and providing a second fluid flow path through the aperture of the first hollow connector body, the second fluid transfer aperture of the fluid transfer member, and the aperture of the second hollow connector body when the fluid transfer member is in the second fluid transfer position, in contact with: (B) a second connector comprising (a') a first hollow connector body having an inner face including a slot, and an outer face, the first hollow connector body having an aperture passing through the inner face and the outer face; (b') a second hollow connector body having an inner face including a slot, and an outer face, the second hollow connector body having an aperture passing through the inner face and the outer face; and, (c') a fluid transfer member, interposed between the first hollow connector body and the second hollow connector body, wherein the fluid transfer member is slidably arranged in the slot of the inner face of the first hollow body and the slot of the inner face of the second hollow body to provide slidable movement between a first fluid transfer position and a second fluid transfer position, the fluid transfer member having a first surface facing the slot of the inner face of the first hollow body and a second surface facing the slot of the inner face of the second hollow body, and having a first fluid transfer aperture passing through the first surface, and a second fluid transfer aperture passing through the first surface and the second surface; the fluid transfer member having a first open end and a second closed end, wherein the first open end is in fluid communication with the first fluid transfer aperture, without fluid communication with the second fluid transfer aperture, providing a first fluid flow path through the first open end and the first fluid transfer aperture when the fluid transfer member is in the first fluid transfer position; and providing a second fluid flow path through the aperture of the first hollow connector body, the second fluid transfer aperture of the fluid transfer member, and the aperture of the second hollow connector body when the fluid transfer member is in the second fluid transfer position, the method further comprising contacting the outer face of the first hollow connector body of the second connector with the outer face of the second hollow connector body of the first connector to provide a first contacting position, twisting the first hollow connector body of the second connector and/or the of the second hollow connector body of the first connector to provide a second contacting position to provide an activating position, sliding the fluid transfer member in the first connector to the second fluid transfer position while the fluid transfer member in the second connector is in the first fluid transfer position.

In a preferred aspect of the method, the method further includes passing fluid along the second fluid flow path through the first connector and through the first fluid flow path of the second connector. Aspects of methods for processing fluid can comprise passing the fluid through any number of connected connectors and/or connector assemblies.

Advantageously, two or more connectors and/or connector assemblies according to aspects of the invention can be connected to extend the number of operations (multiple sterile connections through the same initial connection). As a result, the number of possible leak points in the flow path are reduced (no need to replace manifold, fewer junctions for the same given number of connections), also reducing the size of complexity of the overall manifold. An operator has the choice to use as many connector assemblies as needed for the process, without relying upon complex arrangements of connectors, conduits, T- and Y-connectors, and external hardware such as valves and/or controllers.

Preferably, the connector or connector assembly is a genderless connector assembly, i.e., not requiring male and female connections. Advantageously, a connector or connector assembly can be connected to another connector or connector assembly, for example, a connector assembly as described herein, or as described in U.S. Pat. No. 10,247,342.

In a preferred aspect, a method for processing fluid comprises passing the fluid through the connected connectors and/or connector assemblies.

Aspects of the invention are also suitable for single use technology (SUT) applications.

Each of the components of the invention will now be described in more detail below, wherein like components have like reference numbers.

Figure 1B:
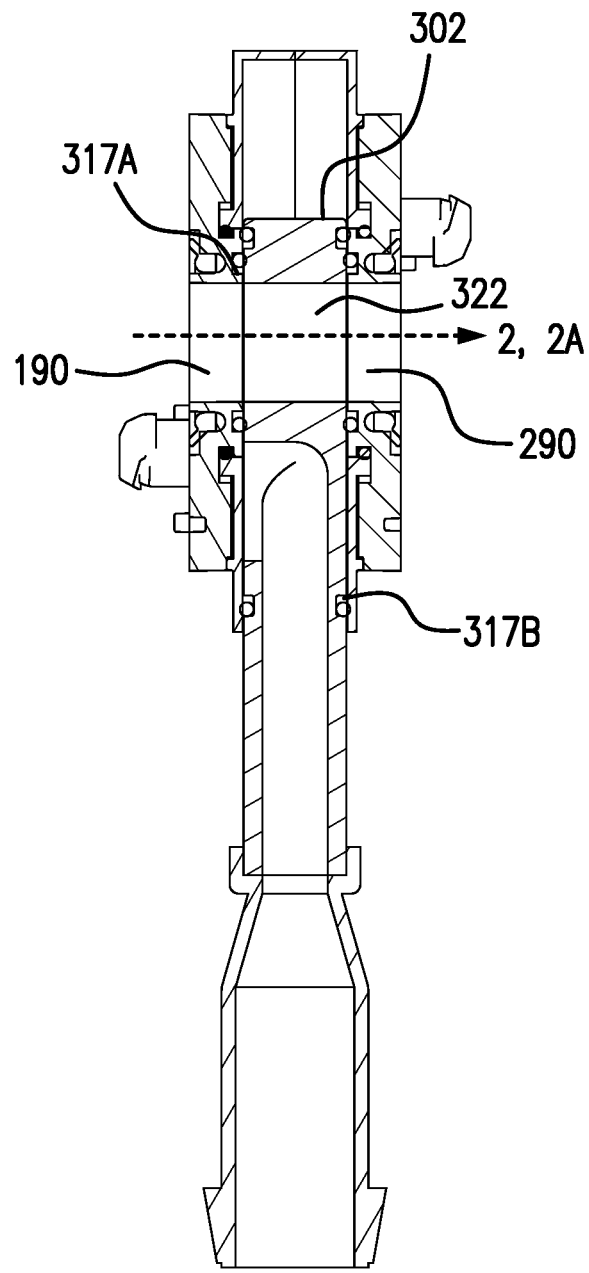
Figure 1C:
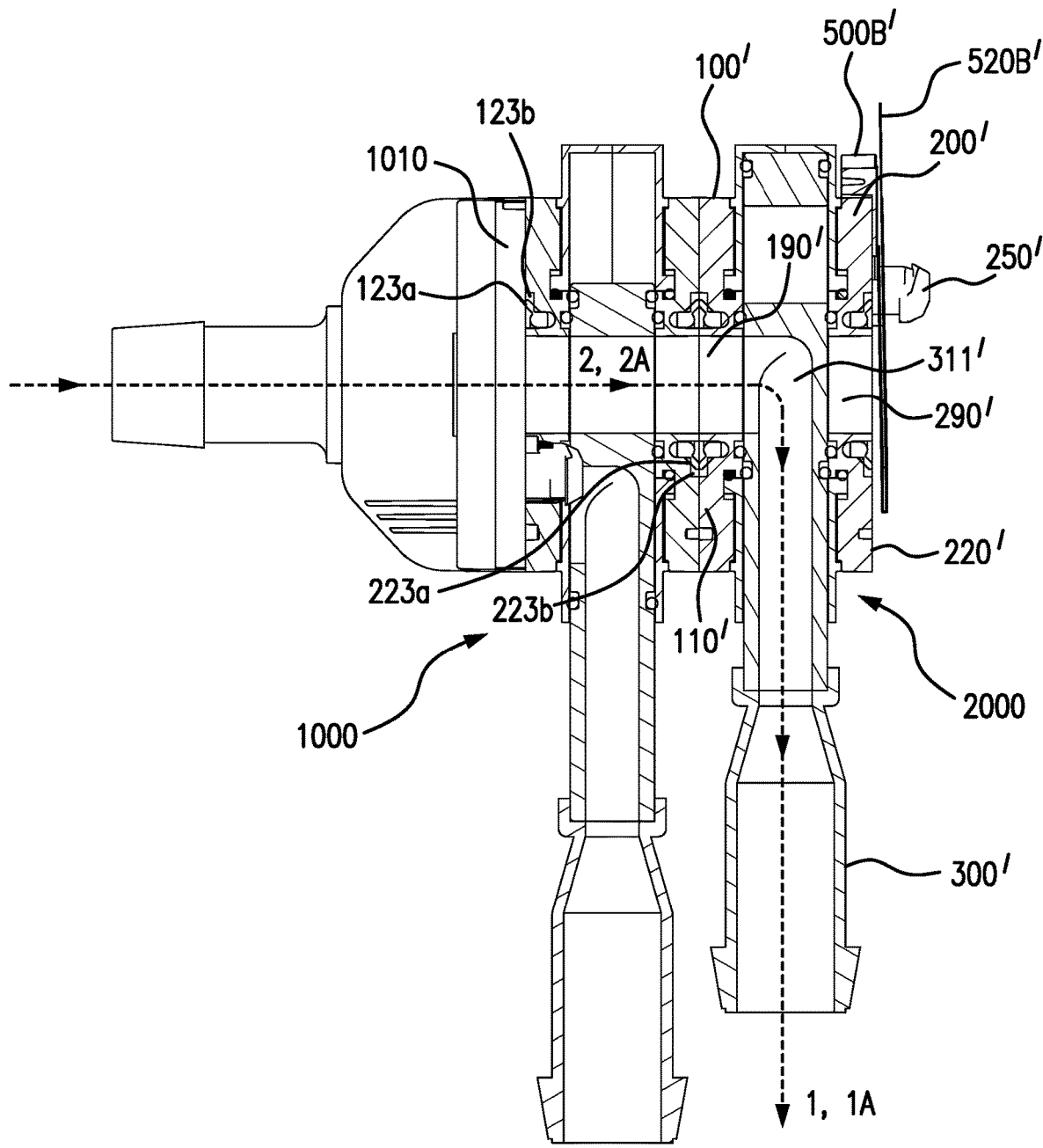
Figure 5A:
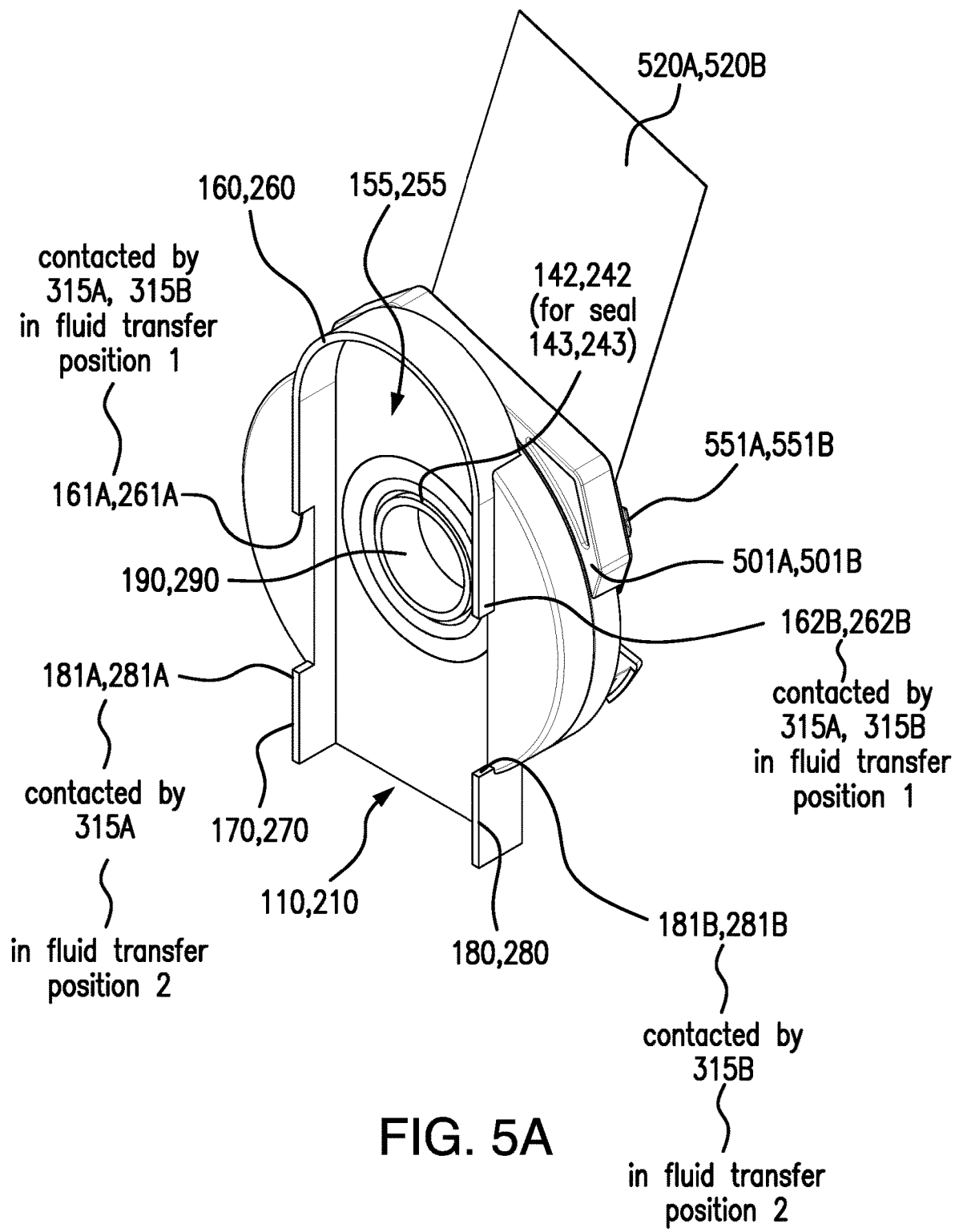

FIGS. 1A and 1B show an aspect of a connector 1000 comprising (a) a first hollow connector body 100 having an inner face 110 including a slot 155, and an annular groove 142 for receiving seal 143 (see also, FIGS. 5A-5B), and an outer face 120 including an annular groove 122 receiving a resilient seal 123 (preferably, a resilient deformable seal including a flexible lip 123a; see also, FIG. 1C (including chamber 123b for lip 123a) and FIG. 3), the first hollow connector body having an aperture 190 (surrounded by annular grooves 143 and 122) passing through the inner face and the outer face; (b) a second hollow connector body 200 having an inner face 210 including a slot 255, and an annular groove 242 for receiving seal 243 (see also, FIGS. 5A-5B) and an outer face 220 including an annular groove 222 receiving a resilient seal 223 (preferably, a resilient deformable seal including a flexible lip 223A; see also, FIG. 1C (including chamber 223b for lip 223b) and FIG. 3), the second hollow connector body having an aperture 290 (surrounded by annular grooves 243 and 222) passing through the inner face and the outer face; the first hollow connector body having an end 125 sealingly contacting end 225 of the second connector body; and, (c) a fluid transfer member 300, interposed between the first hollow connector body and the second hollow connector body, wherein the fluid transfer member is slidably arranged in the slot of the inner face of the first hollow body and the slot of the inner face of the second hollow body to provide slidable movement between a first fluid transfer position 1 (FIG. 1A) and a second fluid transfer position 2 (FIG. 1B), the fluid transfer member having a first surface 310A facing the slot of the inner face of the first hollow body and a second surface 310B facing the slot of the inner face of the second hollow body, and having a first fluid transfer aperture 311 passing through the first surface, and a second fluid transfer aperture 322 passing through the first surface and the second surface; the fluid transfer member having a first open end 301 and a second closed end 302, wherein the first open end is in fluid communication with the first fluid transfer aperture, without fluid communication with the second fluid transfer aperture (blocked by solid wall 313 and solid section 314), providing a first fluid flow path 1A (FIG. 1A) through the first open end and the first fluid transfer aperture when the fluid transfer member is in the first fluid transfer position; and providing a second fluid flow path 2A (FIG. 1B) through the aperture of the first hollow connector body, the second fluid transfer aperture of the fluid transfer member, and the aperture of the second hollow connector body when the fluid transfer member is in the second fluid transfer position.

Typically, the first and second hollow connector bodies 100, 200 are identical, thus reducing cost.

The second fluid transfer position 2 and the second fluid flow path 2A are utilized with respect to the first connector after the first connector and an additional (second) connector are connected and pull-out strips 520A, 520B are removed (see, FIGS. 1A and 1C, wherein, in FIG. 1C, the structures in second connector 2000 labeled with a "'" correspond to the structures without the "'" in first connector 1000, the first connector including an inlet nipple 1010 with an inlet port 1010a), allowing the next first fluid transfer position 1', and the next first fluid flow path 1A' to be utilized with respect to the second connector.

As discussed in more detail below, when the first connector is connected to the second connector, a locking mechanism on the outer face of the second hollow connector body of the first connector is placed in contact with a locking mechanism on the outer face of the first hollow connector body of the second connector, such that the locking mechanisms are in a first contacting position. Preferably, an anti-actuation assembly 500 comprising at least one peel strip was interposed between the locking mechanisms (more preferably, an anti-actually assembly comprising subassembly 500A associated with one hollow connector body and subassembly 500B associated with the other contacting hollow connector body), and the assembly is removed. Subsequently, the second hollow connector body of the first connector and/or the first hollow connector body of the second connector are twisted such that the respective resilient seals seal against the hollow connector bodies in a second contacting position, comprising an actuation position.

The hollow connector bodies can be coupled to each other, including using the locking mechanisms and rotation from the first contacting position to the second contacting (actuation or activation) position, as disclosed in U.S. Pat. No. 10,247,342.

Any number of connectors and/or connector assemblies can be joined, and each additionally joined connector or connector assembly will be initially utilized with the respect to the first fluid transfer position, and the first fluid flow path, via the second fluid transfer position and the second fluid flow path through the connector or connector assembly connected to the new (additional) connector or connector assembly. Thus, for example, using the aspect shown in FIGS. 1C and 2C for reference, an additional (e.g., third) connector can be connected to the outer face 200' of second connector 2000, and, after placing the hollow bodies in the actuation position, subsequently receiving fluid along the second fluid flow path from the second connector after the fluid transfer member 300' is moved to the second fluid transfer position, and, with the fluid transfer member in the third connector in the first position, passing fluid along the first flow path.

Using the aspects shown in FIGS. 4B-4D and 5A for reference, the fluid transfer member 300 has pins 315A, 315B that prevent further slidable movement in the first and second positions in slots 155, 255 contacting the ends 161A, 261A, 162B, 262B of wall section 160, 260 in the first position, and when contacting ends 181A, 281A, 181B, 281B of well sections 170, 270, 180, 280 in the second position.

Figure 2A:
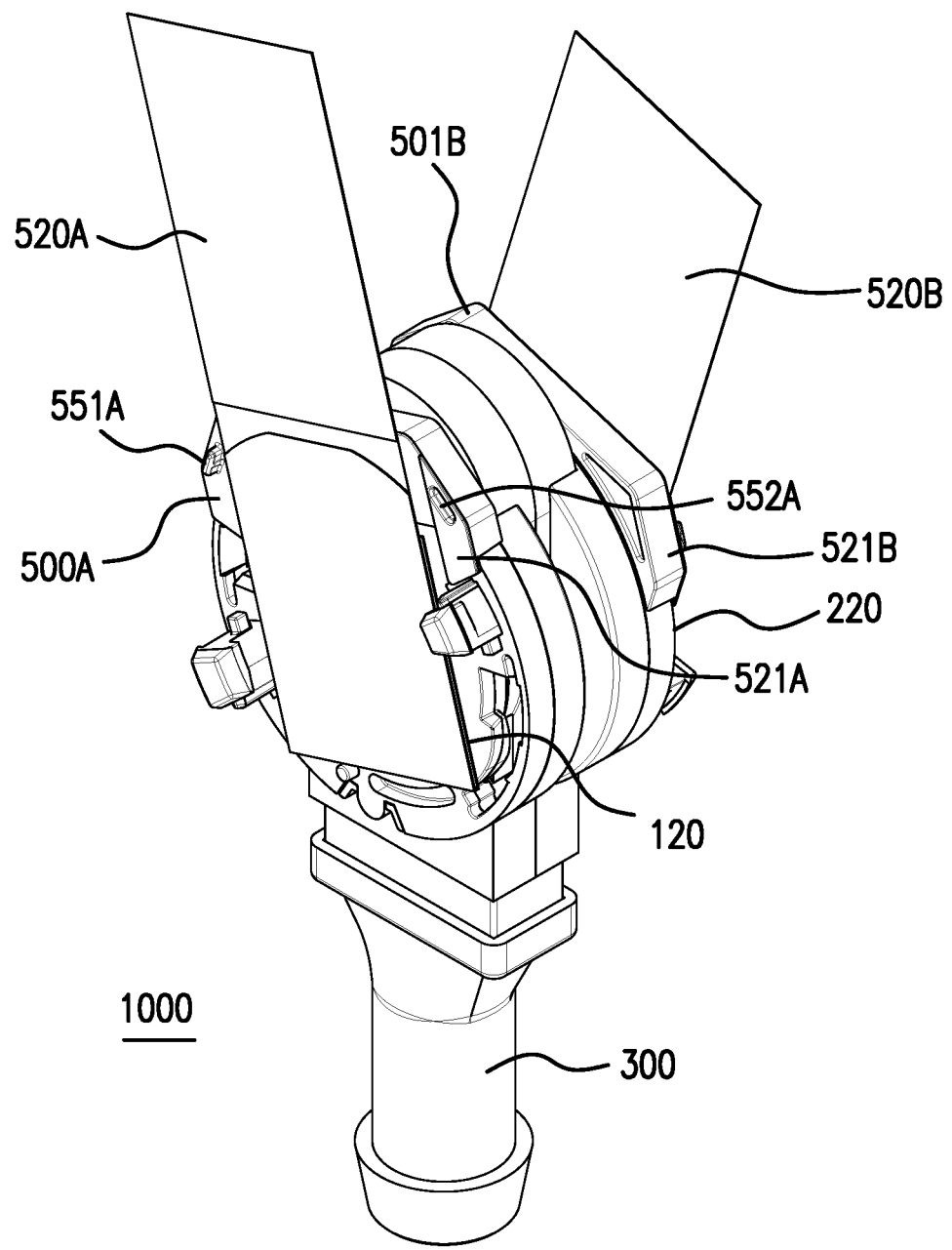
Figure 2B:
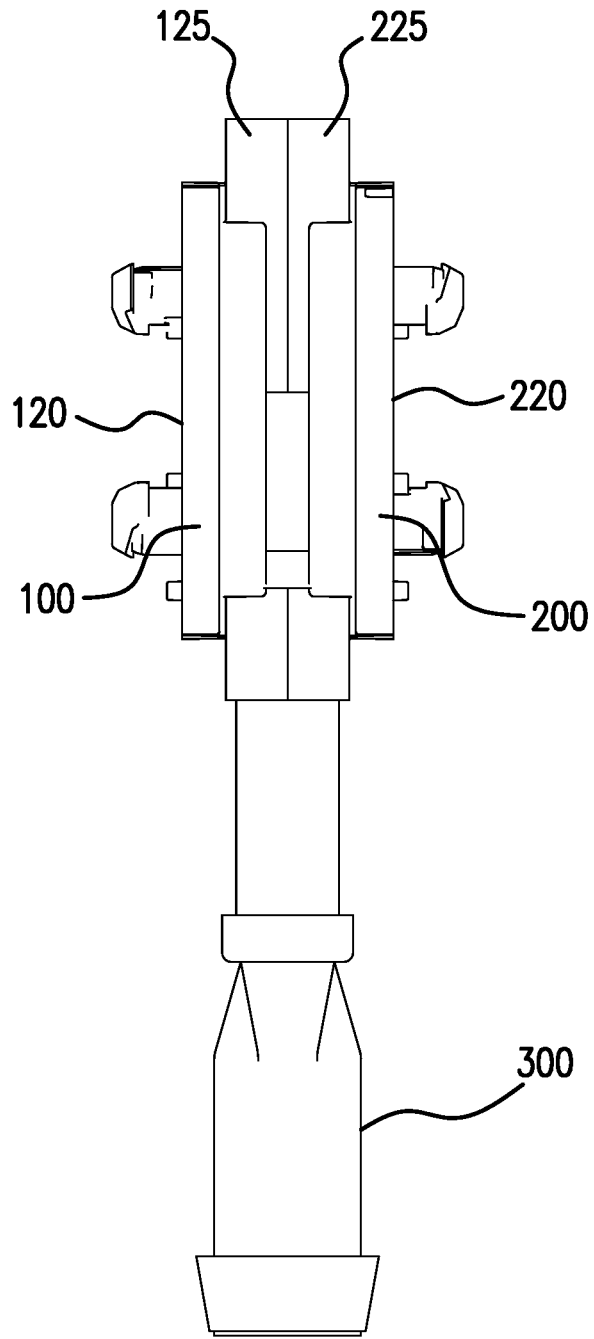
Figure 2C:
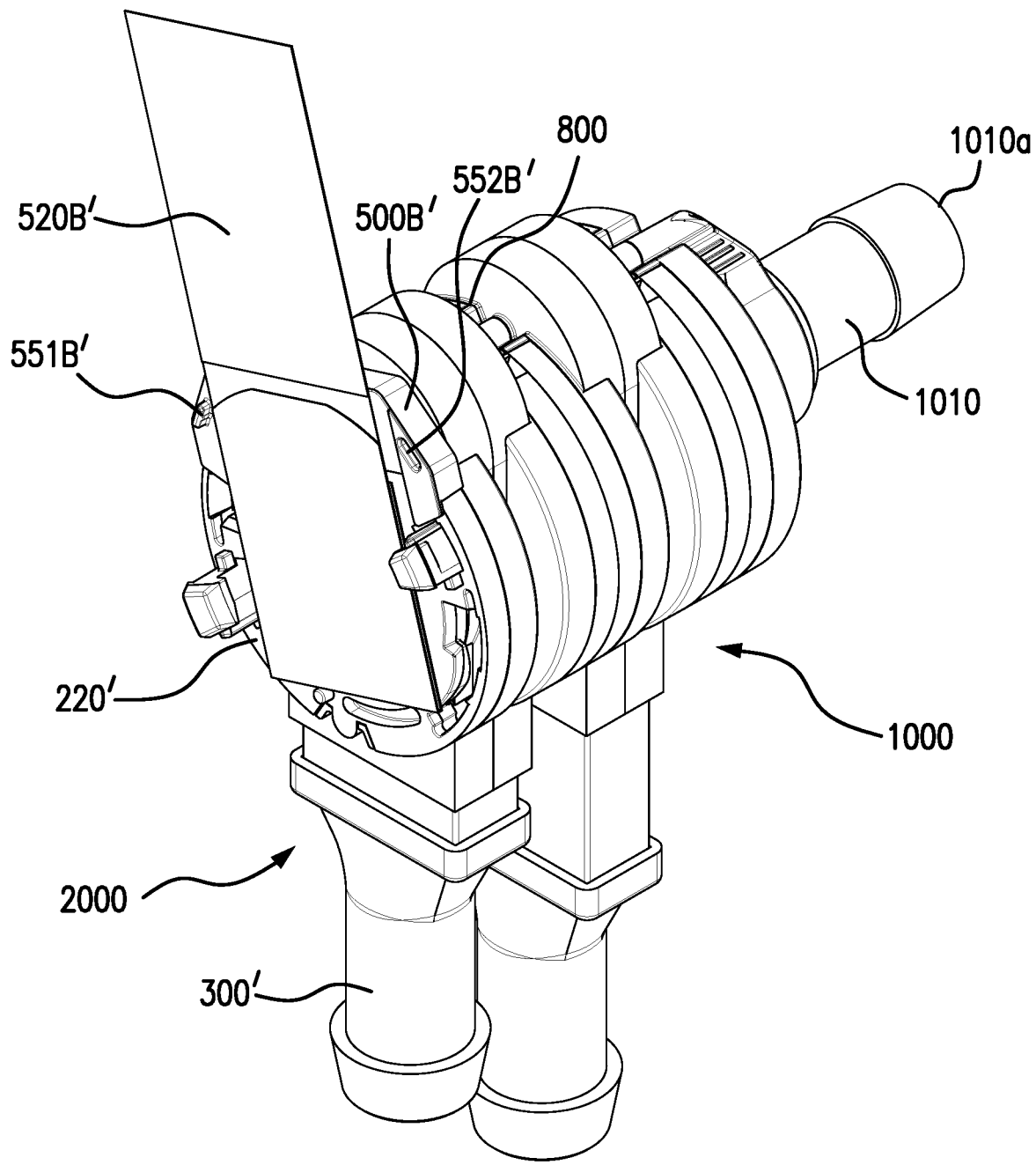
Figure 2D:
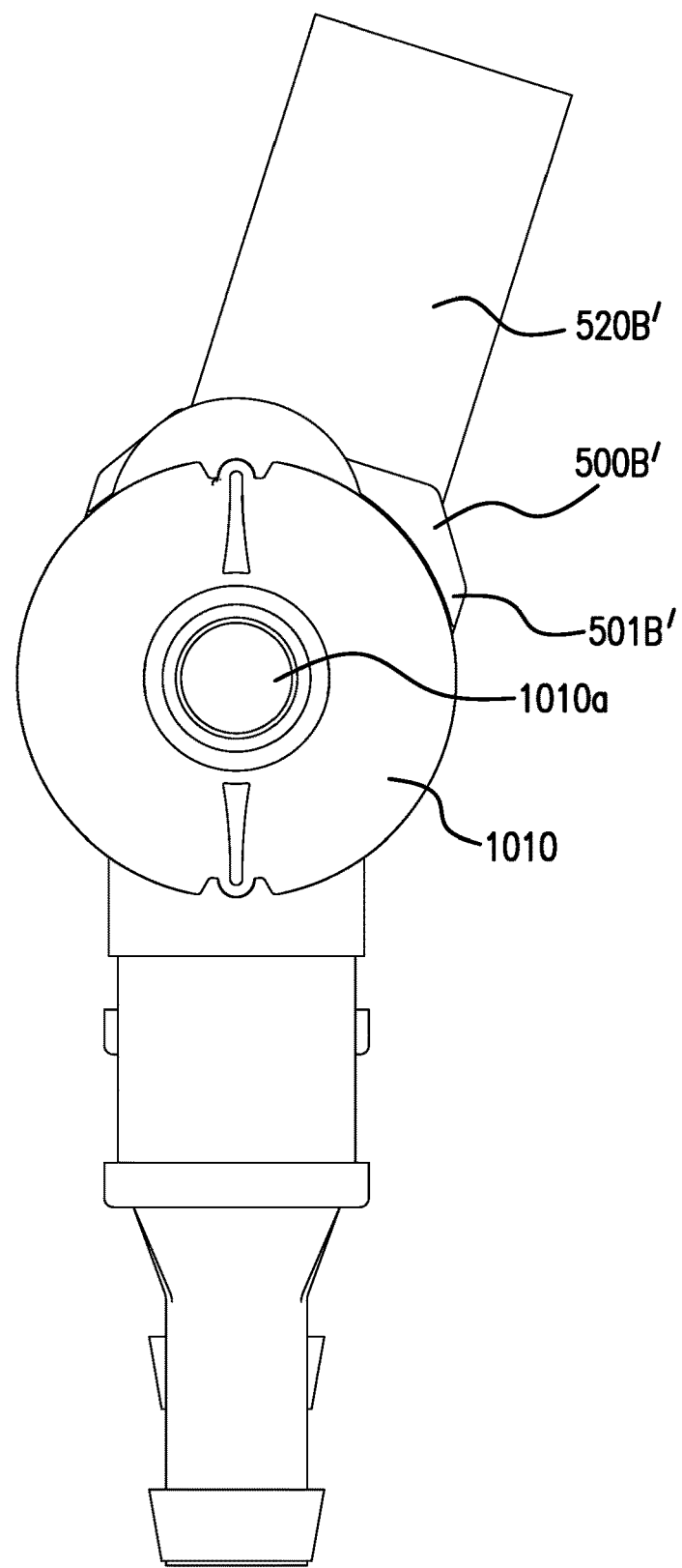

In a preferred aspect of the connector (see, FIGS. 2A, 3 (in particular), 5A, and 5C), the outer faces 110, 220 of the first and second hollow connector bodies each include respective locking mechanisms (first locking mechanism 150; second locking mechanism 250), the respective locking mechanisms comprising a lug 151, 251 extending above the face, the lug including a slot 152, 252, and a guide 153, 253; and a ramp 155, 255 extending below the face. In some embodiments, the locking mechanisms each include a guide 153, 253 on the lug, and a spring arm 159, 259. In the aspect illustrated in FIG. 3, the first connector body includes first locking mechanisms 150A, 150B, including lugs 151A, 151B, slots 152A, 152B, guides 153A, 153B, ramps 155A, 155B, and spring arms 159A, 159B; and the second connector body includes second locking mechanisms 250A, 250B, including lugs 251A, 251B, slots 252A, 252B, guides 253A, 253B, ramps 255A, 255B, and spring arms 259A, 259B. The locking mechanism is integrally formed with the body, and as such, does not move separately from the rest of the body when the body moves from the first position to the second position. It should be understood that for ease of reference, while FIGS. 1A, 2A and 3 show locking mechanisms 150, 250, and subassemblies 500A, 500B on the outer faces of the first and second hollow bodies of first connector 1000, when connecting two connectors together, the locking mechanism of the hollow connector body of one connector contacts the locking mechanism of the hollow connector body of the other connector, with anti-actuation assembly 500 (subassemblies 500A, 500B including respective peel strips 520A, 520B) interposed between the locking mechanisms.

The anti-actuation assembly, when present, prevents forming the actuation position between connectors or connector assemblies, and when removed, allows forming the actuation position of the connectors or connector assemblies assembly. If desired, the assembly, or each sub-assembly, can include a pull ring.

After an anti-actuation assembly 500 is removed, either or both of the contacting hollow connector bodies can be rotated from a first position such that the ramp(s) of the locking mechanism(s) of one hollow connector body engages with the slot(s) in the lug(s) of the locking mechanism(s) of the other hollow connector body, until the hollow bodies are in a second (actuation) position. Once the hollow connector bodies are in the actuation position, the interiors of the connector bodies fluidly communicate with one another through the respective coaxially aligned apertures 290, 190', preferably, in a sterile manner free of any external contamination.

Figure 3A:
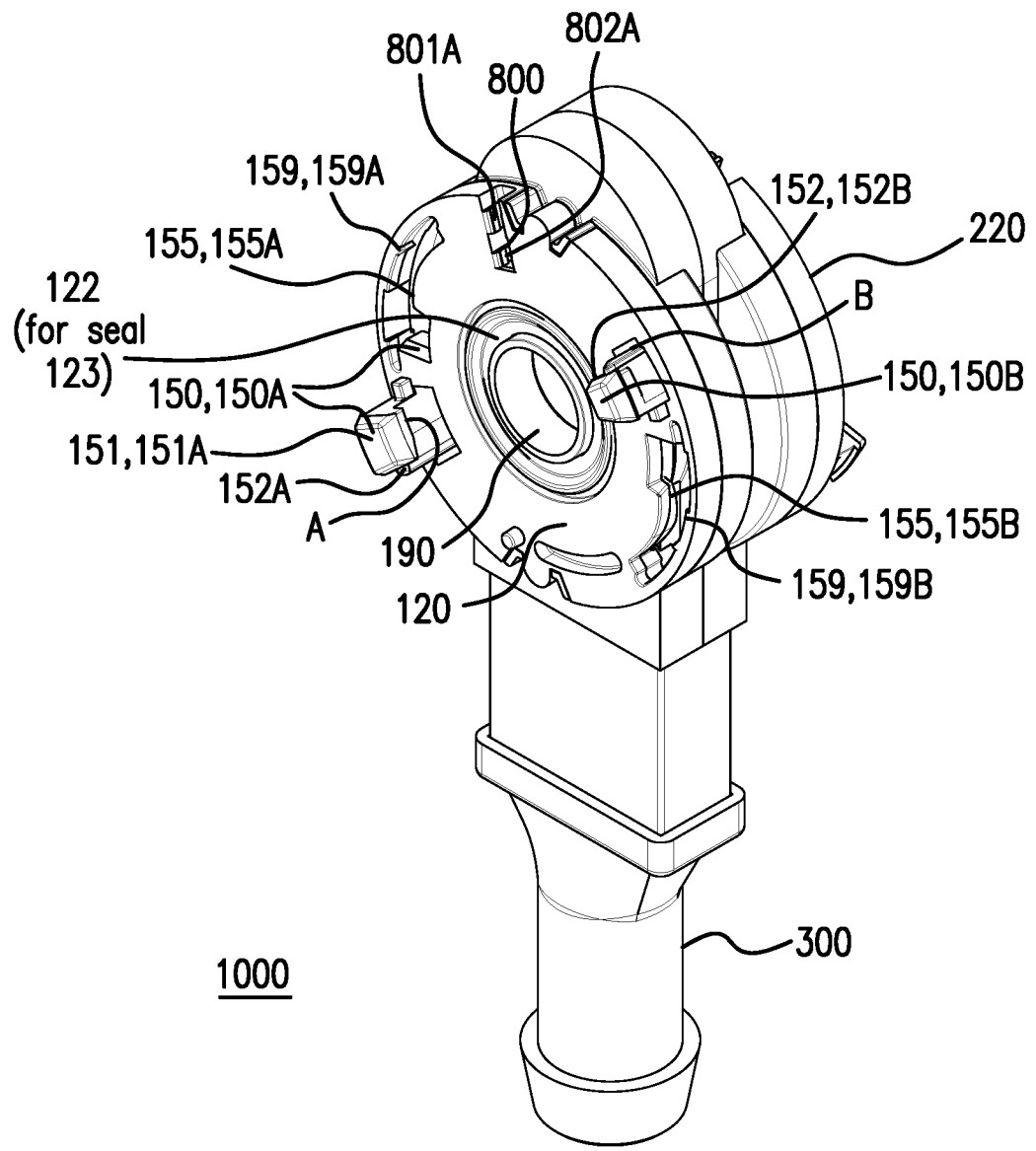
Figure 5B:
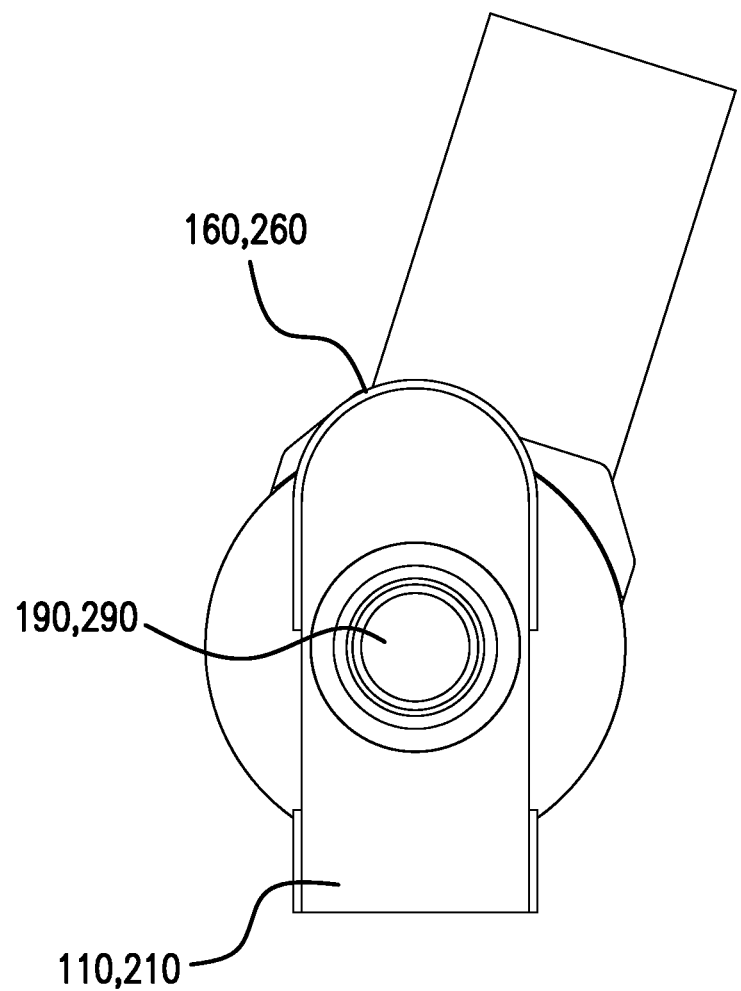

Optionally, (a) the surface of the ramp and the surface of the slot that will contact the surface of the ramp have initial angles, and then level, such that the lugs stop on a level surface, providing a desired amount of pressure on the main bodies of the seals, when the connector bodies are in the actuation position, and/or (b), as shown particularly in FIGS. 3 and 5B, the locking mechanism has a spring arm 159 (159A, 159B), 259 (259A, 259B) that flexes to allow the lug guide 153 (153A, 153B), 253 (253A, 253B) to deflect it and return once the lug has passed, retaining the lug in the actuation position, preferably while providing a tactile and/or audible "click." Using FIG. 3A for reference, "A" and "B" indicate where the spring arm has returned after flexing, providing a tactile and/or audible "click."

In some embodiments, each connector or connector assembly comprises an alignment arrangement for mating the anti-actuation assembly with the first connector hollow body and the second hollow connector body, the alignment arrangement comprising protrusions and recesses; wherein the first and second surfaces of the anti-actuation assembly, the first hollow connector first body end, and the second hollow connector first body end each have at least one protrusion and/or at least one recess, such that the first surface of the anti-actuation assembly mates with the first hollow connector body face, and the second surface of the anti-actuation assembly mates with the second hollow connector body face.

Figure 3B:
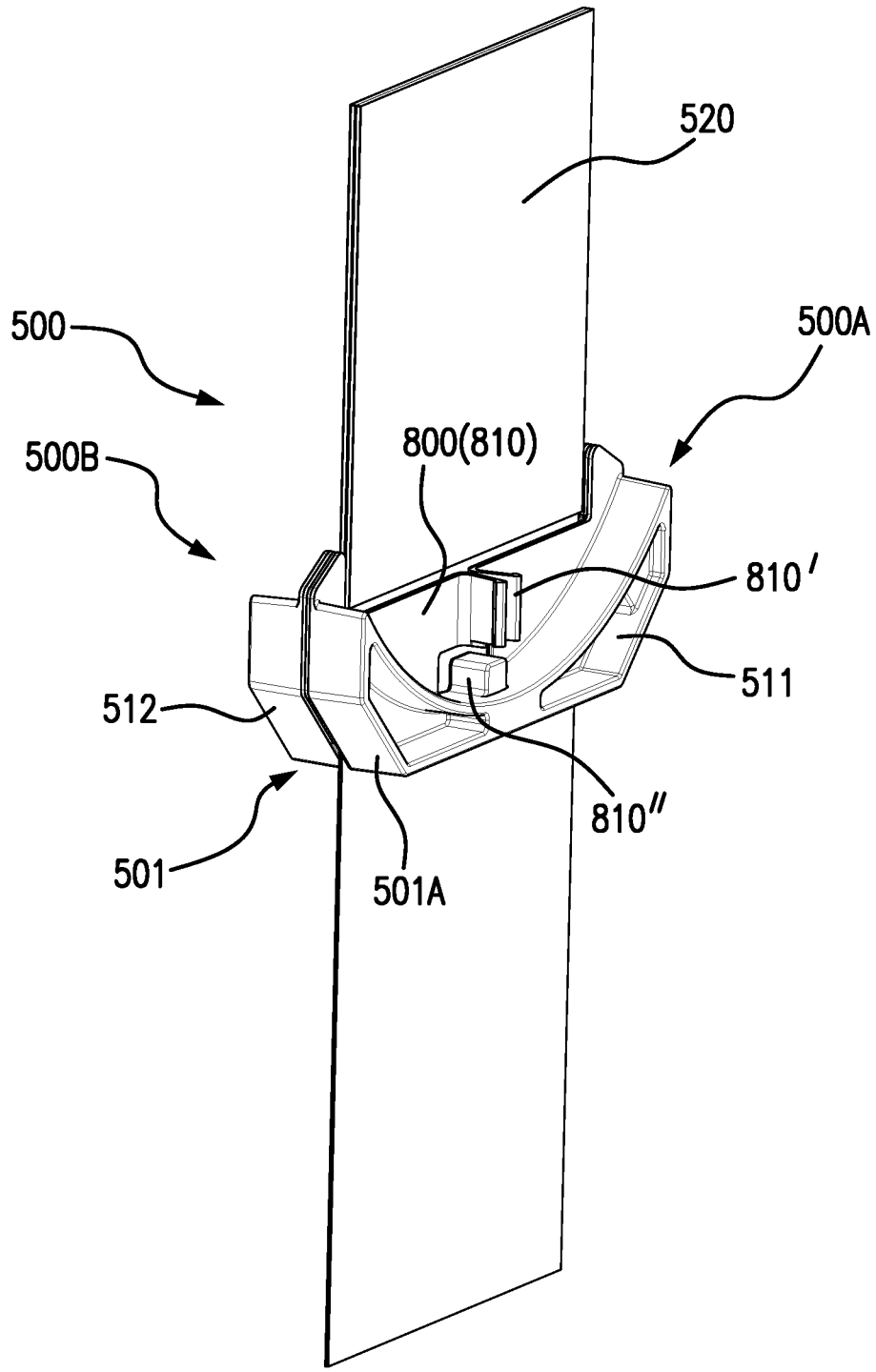
Figure 4A:
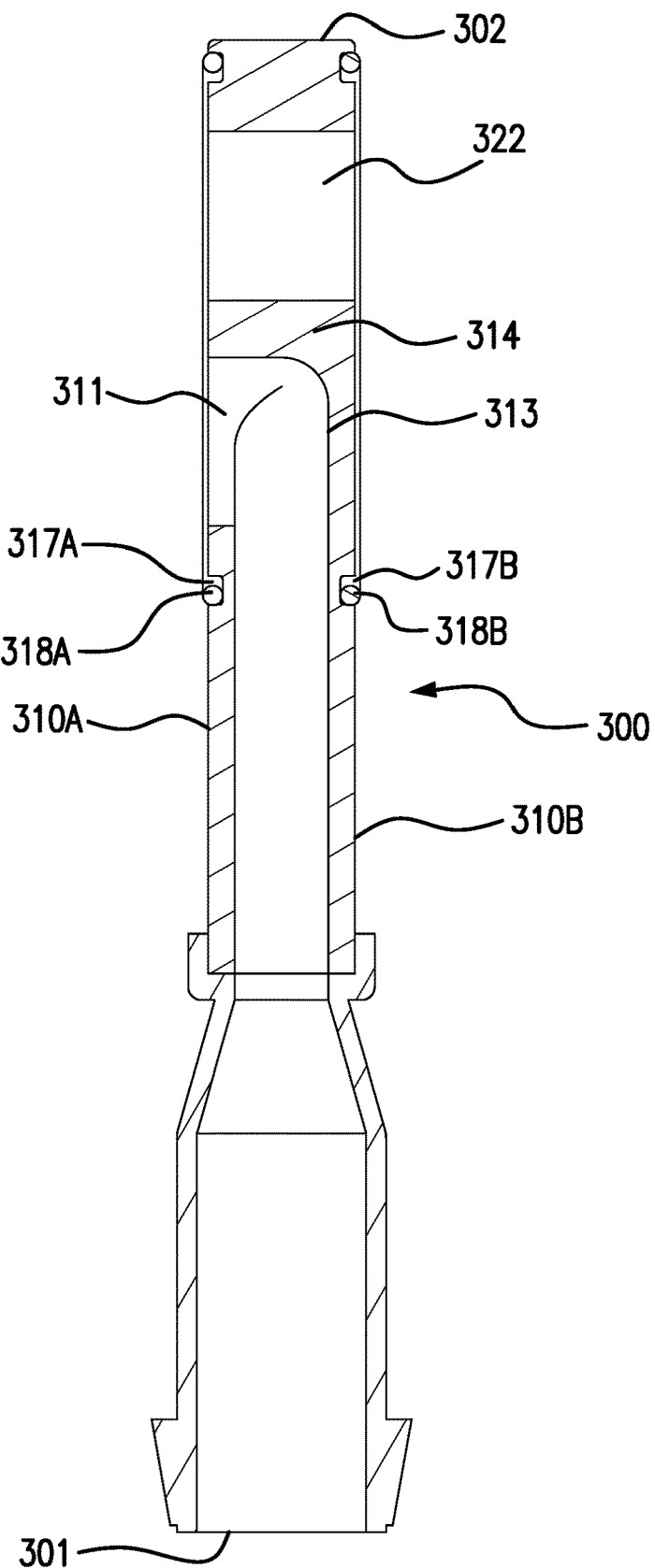
Figure 4B:
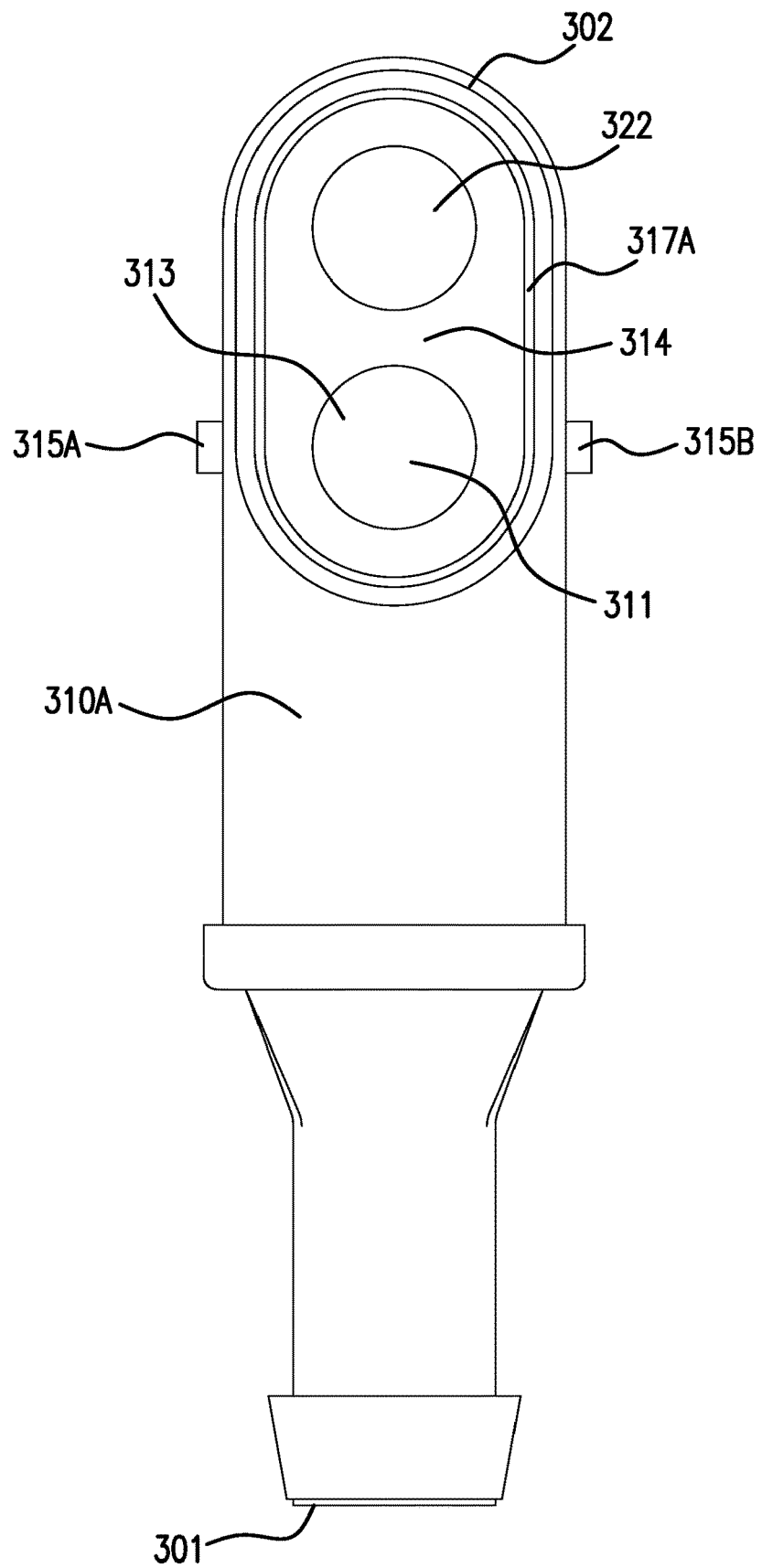
Figure 4C:
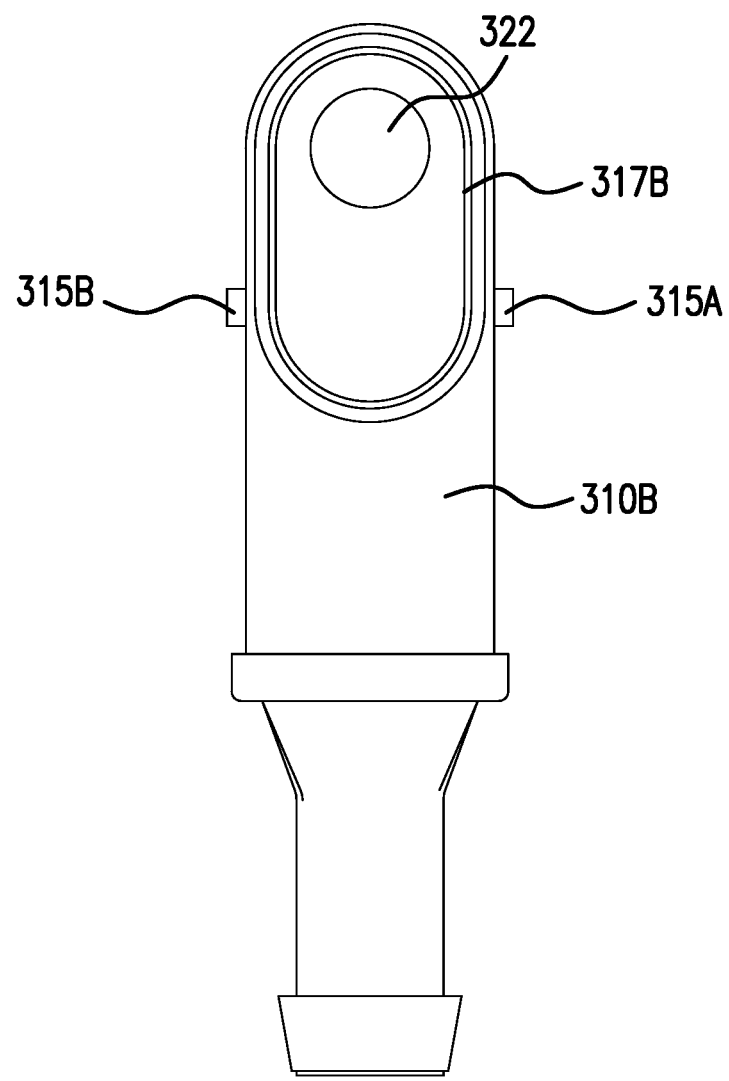
Figure 4D:
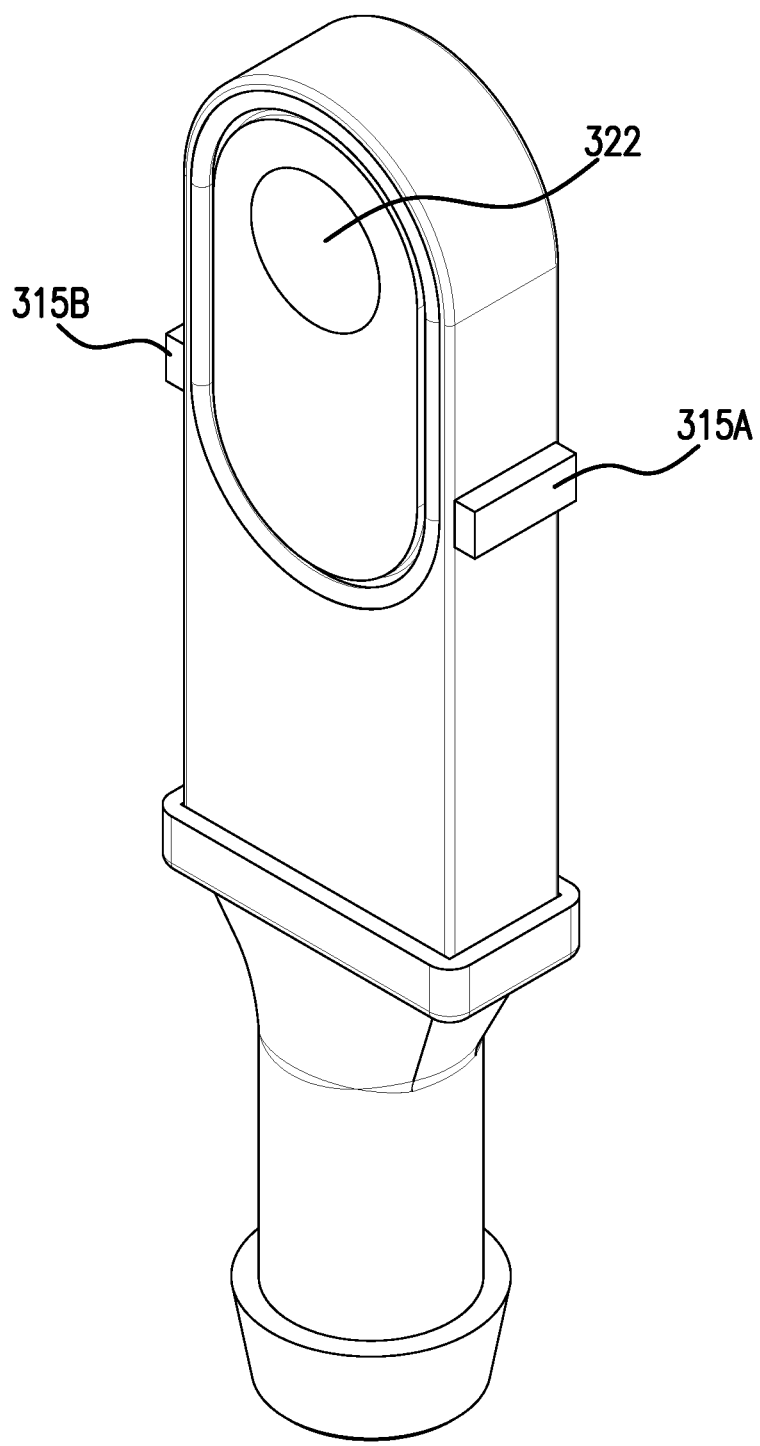
Figure 4E:
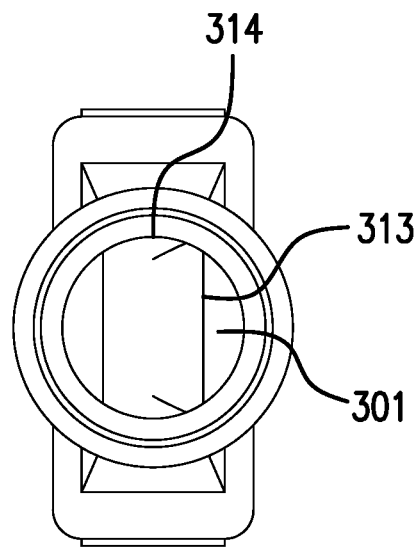
Figure 4F:
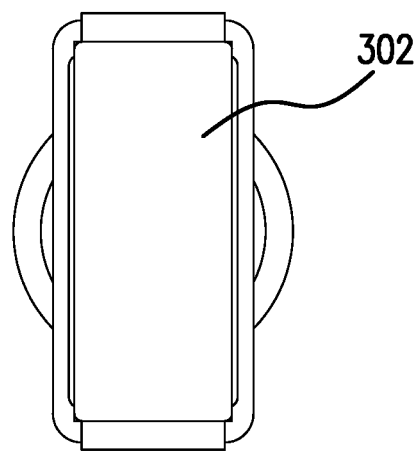

For example, in the aspect shown in FIGS. 3A and 3B, the connector further comprises an alignment arrangement 800, including a recess 801 illustrated with 2 slots (801a and 802b) in the face 110 of the first hollow connector body and a protrusion 810 (shown as having 2 snap hooks 810' and a pin 810") on the first surface 511 of the anti-actuation tab 501, the protrusion being engageable with the recess 801 (wherein the second connector hollow body has the same structure). As discussed below, in aspects including pins, the engagement of the pins with the recesses further reduces flexing/movement when the subassemblies are engaged with the respective hollow bodies.

Figure 5C:
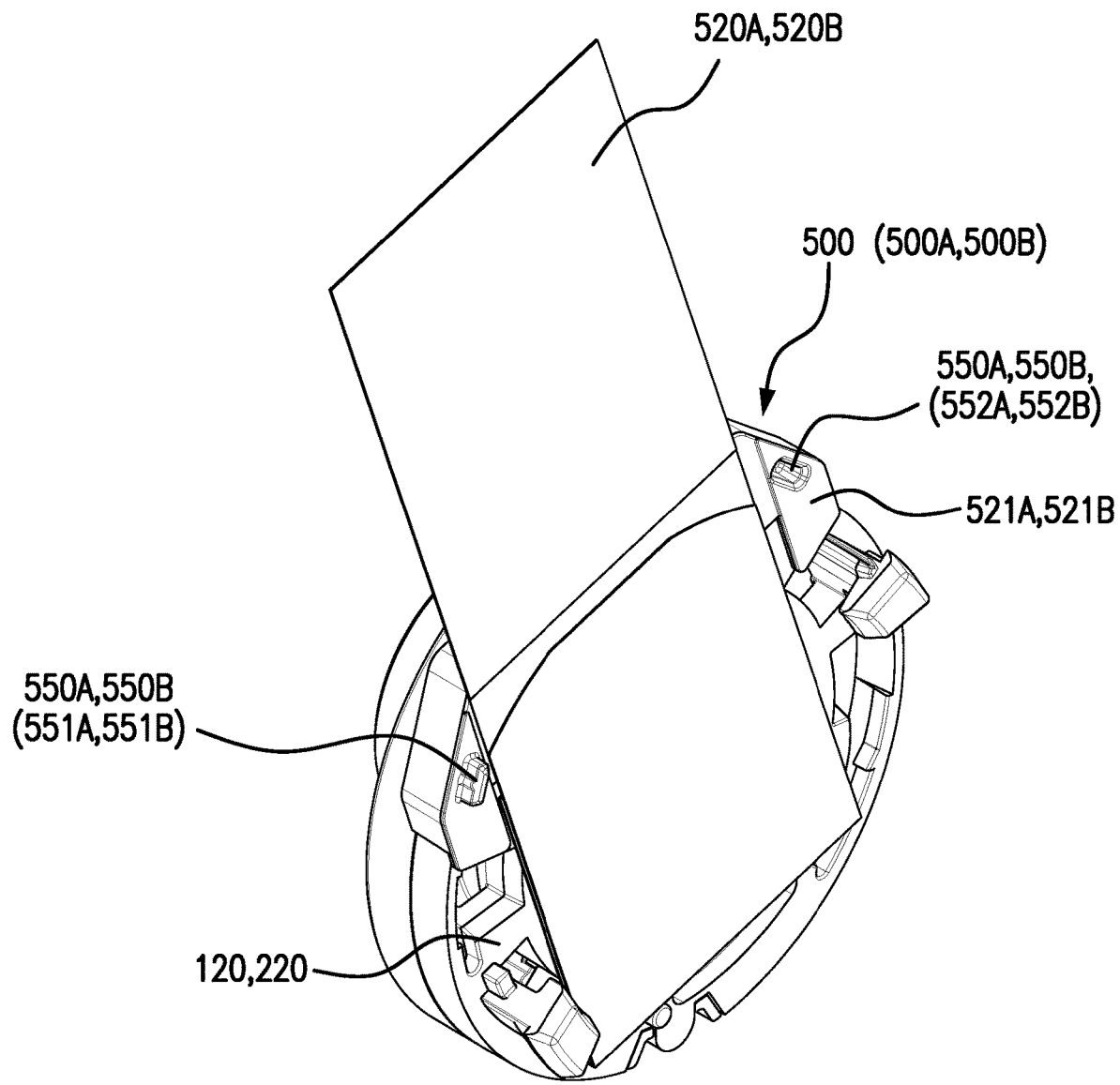
Figure 6A:
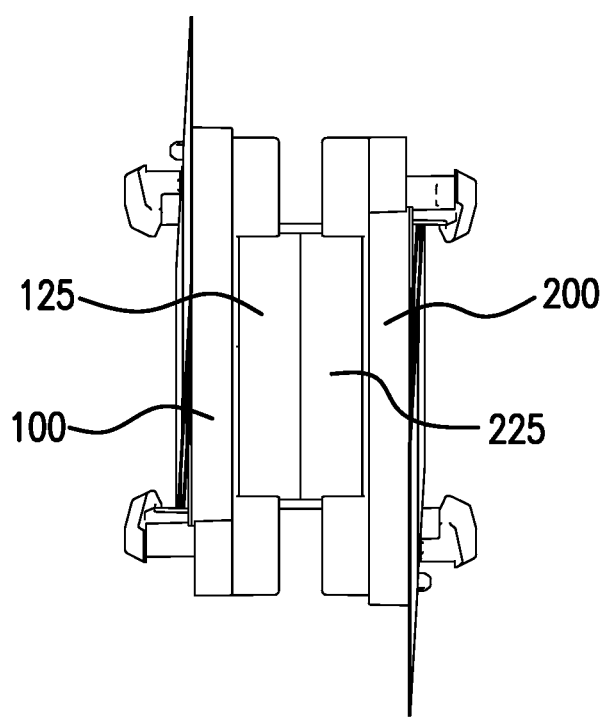
FIGS. 6A and 6B are drawings showing, respectively, top and bottom views of the first connector shown in FIG. 2A.
Figure 6B:
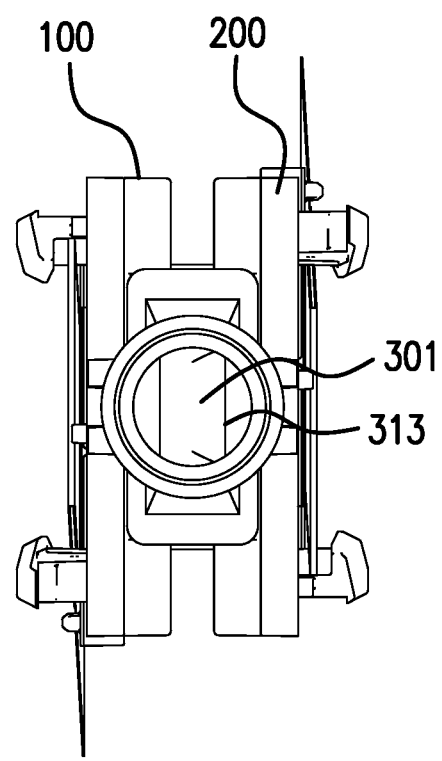

If desired, each subassembly 500A, 500B can comprise a keying arrangement comprising at least one protrusion and at least one recess so that the first anti-actuation subassembly and the second anti-actuation subassembly can be mated together when the hollow connector bodies contact each other in the first position. For example, as shown in FIG. 5C, subassemblies 500A, 500B includes respective keying arrangements 550A, 550B comprising protrusions 551A, 551B, and recesses 552A, 552B wherein protrusion 551A can be mated with recess 552B, and protrusion 551B and be mated with recess 551A. Advantageously, this allows the operator to pull either or both subassemblies and/or either or both peelable strips 520A, 520B and remove the anti-actuation assembly from the connectors or connector assembles, so that the hollow connector bodies can be placed in the actuation position.

In some aspects, the integrally formed locking mechanism and anti-actuation assemblies and their operation can be as described in U.S. Pat. No. 10,247,342.

To enhance the sterility of the interiors of the connector bodies, peel strips (seal layers) are preferably arranged to cover the openings at the outer faces of the connector hollow bodies. The peel strips may be variously configured. Typically, the peel strip(s) are joined (e.g., welded, trapped, or clamped) to the anti-actuation assembly tab(s) and/or the faces of the hollow connector bodies. Preferably, peel strips are joined to the respective subassembly tabs and the hollow connector body faces (also covering the seals and contacting the seal lips). For many embodiments, the peel strip(s) may also cover all or at least a portion of the face seals without being joined to the seals. For example, each peel strip may completely cover at least the seal closest to the openings. The peel strip may not be joined to the seals themselves but may be joined to the surface of the face surrounding each seal.

The peel strip may be made from an impermeable material or a permeable material that resists the passage of contaminants, including biological containments. These materials include, but are not limited to, elastomeric sheets, polymeric films, and metal foils, e.g., aluminum foil, any of which may further include a reinforcing material. Further, the peel strip may be coated and/or impregnated with a biocide. Preferably, the peel strip is a sterile porous or microporous membrane, allowing steam to pass through during autoclaving, in some aspects having a minimum tensile strength of about 60N.

Any of numerous seals may be provided on the face, including, for example, gaskets, resilient sealing members, or O rings. Preferably, the seal comprises a soft rubber or thermoplastic elastomer (TPE) (e.g., about 50 to about 65 shore A). The flexible seal lips 123A, 223A (if present) can assist in preventing environmental contamination from entering the connector assembly when the anti-actuation assembly is removed. Since the lips can flex and spring, the peel strips can be removed with reduced force, and the lips quickly close the gap. As the hollow connector bodies are moved (e.g., twisted) into the actuation position, the flexible lips 123a, 223a (that are preferably narrow) quickly fold out of the way into a recess in each hollow connector body face (123b, 223b), wherein both the lips and the seal bodies (seal lozenges) contact each other, providing a more robust face seal, and the contact between the lozenges provides a face to face seal, preventing fluid leaks even under increases pressures (e.g., pressures up to about 4 barg).

In another aspect, a connector assembly is provided, comprising an aspect of the the connector, further comprising a first removable cap, engaged with the first hollow connector body, wherein the removable anti-actuation assembly is interposed between the first removable cap and the first hollow connector body, the first removable cap covering the outer face of the first hollow connector body; and, a second removable cap, engaged with the second hollow connector body, wherein the removable anti-actuation assembly is interposed between the second removable cap and the second hollow connector body, the second removable cap covering the outer face of the second hollow connector body.

Figure 7A:
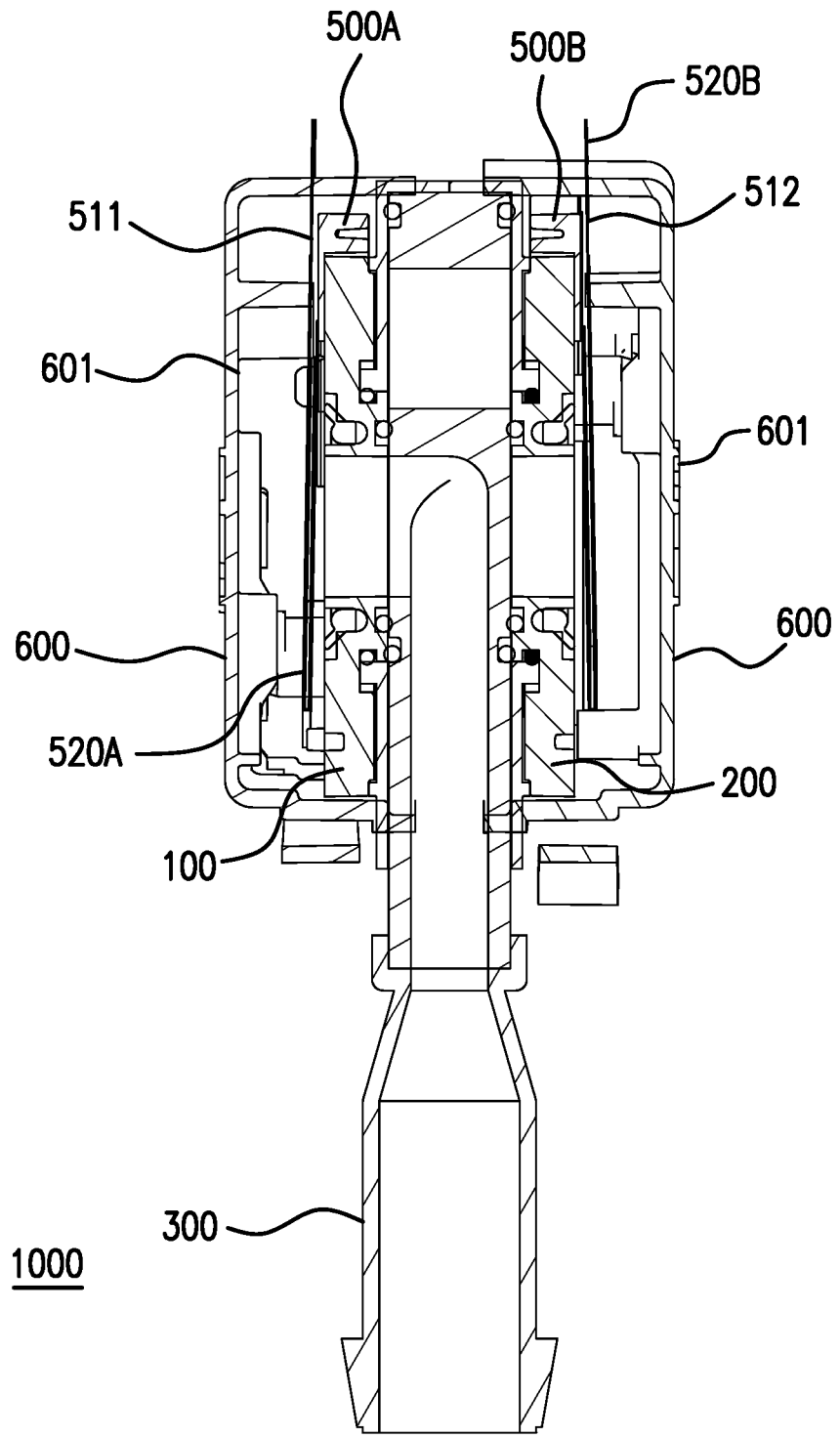
FIG. 7A is a drawing showing a cross-sectional view of a first connector assembly comprising the first connector shown in FIG. 1A according to an aspect of the invention (also showing integrally formed locking mechanisms and removable caps)
Figure 7B:
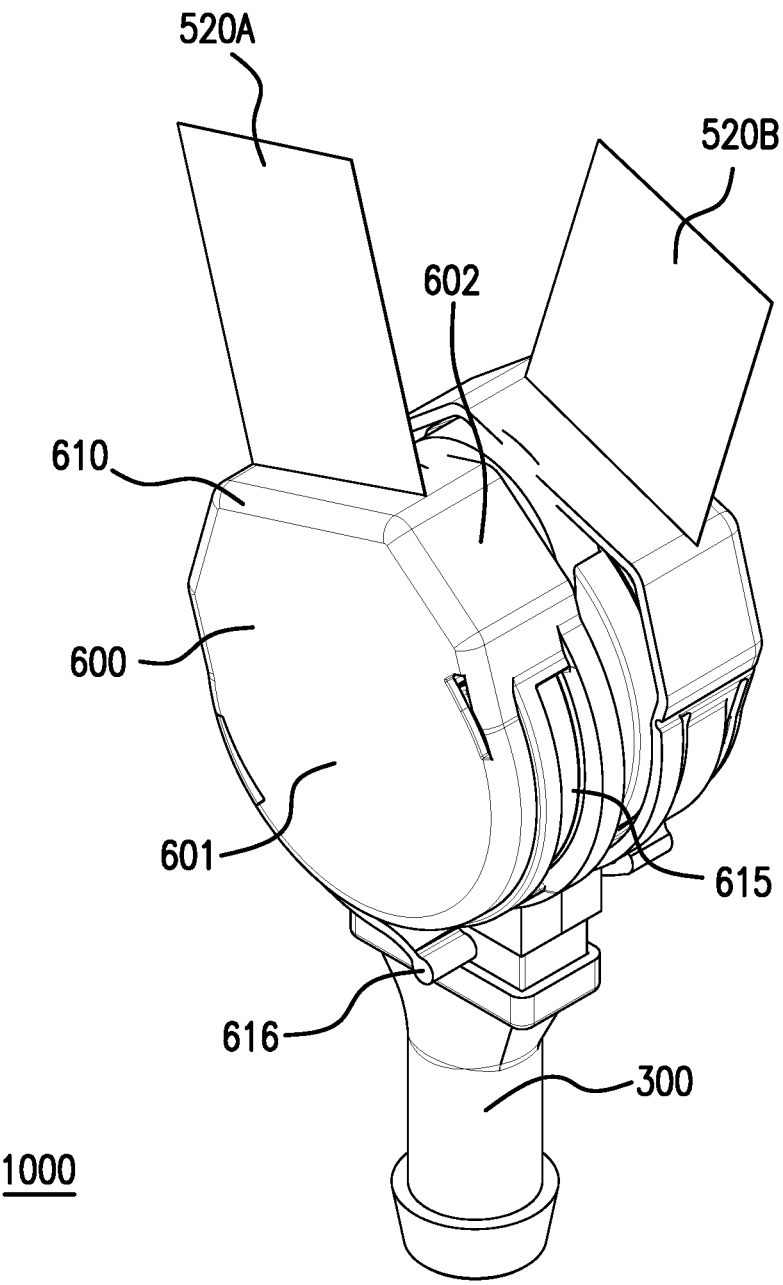
FIG. 7B is a drawing showing a front perspective view of the first connector assembly shown in FIG. 7A.

To prevent inadvertent removal of or damage to the peel strips, each connector body may further comprise a removable cap which covers at least a substantial portion of the peel strip and the first end of the connector body. The cap can be fitted to the connector body at the first end, for example, by a friction fit or a snap fit, and may have any of a wide variety of configurations. For example, as shown in FIGS. 7A, and 7B, each cap 600 (cap 700 on the second connector assembly will have the same structures) may have a rigid top 601 which protects at least part of the peel strip and a skirt 602 which fits along the rim of the connector body 100, 200. The cap 600 may also include handle 610 as part of the skirt, or which extends axially below the skirt 602. Preferably, as shown in FIG. 46B, the cap includes a tear strip 615 having a tear strip handle 616 allowing the operator to grasp the tear strip handle and tear the tear strip, allowing the cap to be more easily removed from the connector body. The peel strip 520 (520A) may be bent axially under the handle 610 and the handle may extend along all or at least a portion of the peal strip 520 (520A). The handle, tear strip, and/or tear strip handled may be used to lift the cap 600 off of the connector body 100 and may also prevent inadvertent manipulation of the anti-actuation assembly tab 501 and/or peel strip.

The components of the connector and connector assembly can be sterilized as is known in the art (e.g., autoclaved, gamma irradiated, etc.)

The components of the connector and connector assembly may be formed from a wide variety of materials. For example, one or more of any one of the following: hollow connector body, locking mechanism, anti-activation assembly and cap, may be made from any metallic material and/or polymeric material which is compatible with the fluid that will flow through the connector assembly. Preferably, the connector bodies, the locking mechanisms, and the caps are made from polymeric material, and the polymeric material may include, but is not limited to, one or more of a polycarbonate, polypropylene, polystyrene, polyvinyl chloride, polyethersulphone, polyvinylidene fluoride, or polysulphone. For some embodiments, a transparent or translucent polymeric material may be selected. Typically, the hollow bodies, hollow tubes, tabs, and connector body covers are formed from a rigid injection molded plastic, preferably a BPA-free plastic, such as polyethersulfone (PES), polycarbonate (PC), polysulfone (PSU), and polybutylene terephthalate (PBT), and the cap is made from a low density injection molded plastic such as TPE or polypropylene (PP).

The components may be fabricated in a variety of ways, including molding, machining, pressing, and stamping, and may be fashioned into subassemblies.

Additionally, or alternatively, some components according to aspects of the invention can be monolithic, for example, manufactured via additive manufacturing (sometimes referred to as "additive layer manufacturing" or "3D printing"). They are typically formed by repeated depositions of a metal powder bound together with an activatable binder (e.g., binder jetting, sometimes referred to as "drop on powder"), typically followed by agglomerating the powder, e.g., by sintering. Some components can be manufactured together via additive manufacturing in a continuous operation at substantially the same time.

Any suitable additive manufacturing equipment can be used, and a variety of production 3D printers are suitable and commercially available.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A connector comprising
   (a) a first hollow connector body having an inner face including a slot, and an outer face, the first hollow connector body having an aperture passing through the inner face and the outer face;
   (b) a second hollow connector body having an inner face including a slot, and an outer face, the second hollow connector body having an aperture passing through the inner face and the outer face;
      wherein the outer face of the first hollow connector body includes a first annular groove with a first resilient deformable annular seal arranged in the first annular groove around the aperture; and the outer face of the second hollow connector body includes a second annular groove with a second resilient deformable annular seal arranged in the second groove around the aperture; and,
   (c) a fluid transfer member, interposed between the first hollow connector body and the second hollow connector body, wherein the fluid transfer member is slidably arranged in the slot of the inner face of the first hollow body and the slot of the inner face of the second hollow body to provide slidable movement between a first fluid transfer position and a second fluid transfer position,
      the fluid transfer member having a first surface facing the slot of the inner face of the first hollow body and a second surface facing the slot of the inner face of the second hollow body, and having a first fluid transfer aperture passing through the first surface, and a second fluid transfer aperture passing through the first surface and the second surface;
      the fluid transfer member having a first open end and a second closed end, wherein the first open end is in fluid communication with the first fluid transfer aperture, without fluid communication with the second fluid transfer aperture, providing a first fluid flow path through the first open end and the first fluid transfer aperture when the fluid transfer member is in the first fluid transfer position; and providing a second fluid flow path through the aperture of the first hollow connector body, the second fluid transfer aperture of the fluid transfer member, and the aperture of the second hollow connector body when the fluid transfer member is in the second fluid transfer position.

2. The connector of claim 1, wherein the first resilient annular seal in the first annular groove and the second resilient annular seal in the second annular groove each have a flexible lip.

3. The connector of claim 2, wherein the outer face of the first hollow connector body includes an integrally formed locking mechanism; the integrally formed locking mechanism comprising at least one lug including a slot, and at least one ramp; and an anti-actuation assembly engagement portion comprising at least one recess and/or at least one protrusion; and,
   the outer face of the second hollow connector body includes an integrally formed locking mechanism; the integrally formed locking mechanism comprising at least one lug including a slot, and at least one ramp; and an anti-actuation assembly engagement portion comprising at least one recess and/or at least one protrusion.

4. The connector of claim 1, wherein the outer face of the first hollow connector body includes an integrally formed locking mechanism; the integrally formed locking mechanism comprising at least one lug including a slot, and at least one ramp; and an anti-actuation assembly engagement portion comprising at least one recess and/or at least one protrusion; and,
   the outer face of the second hollow connector body includes an integrally formed locking mechanism; the integrally formed locking mechanism comprising at least one lug including a slot, and at least one ramp; and an anti-actuation assembly engagement portion comprising at least one recess and/or at least one protrusion.

5. A connector assembly comprising the connector of claim 4, comprising a first removable cap, engaged with the first hollow connector body, wherein the anti-actuation assembly is interposed between the first removable cap and the first hollow connector body, the first removable cap covering the outer face of the first hollow connector body; and,
   a second removable cap, engaged with the second hollow connector body, wherein the anti-actuation assembly is interposed between the second removable cap and the second hollow connector body, the second removable cap covering the outer face of the second hollow connector body.

6. A connector assembly comprising the connector of claim 3, comprising a first removable cap, engaged with the first hollow connector body, wherein the anti-actuation assembly is interposed between the first removable cap and the first hollow connector body, the first removable cap covering the outer face of the first hollow connector body; and,
   a second removable cap, engaged with the second hollow connector body, wherein the anti-actuation assembly is interposed between the second removable cap and the second hollow connector body, the second removable cap covering the outer face of the second hollow connector body.

7. A method for making fluid connections, the method comprising
   (A) placing a first connector comprising (a) a first hollow connector body having an inner face including a slot, and an outer face, the first hollow connector body having an aperture passing through the inner face and the outer face; (b) a second hollow connector body having an inner face including a slot, and an outer face, the second hollow connector body having an aperture passing through the inner face and the outer face; and, (c) a fluid transfer member, interposed between the first hollow connector body and the second hollow connector body, wherein the fluid transfer member is slidably arranged in the slot of the inner face of the first hollow body and the slot of the inner face of the second hollow body to provide slidable movement between a first fluid transfer position and a second fluid transfer position, the fluid transfer member having a first surface facing the slot of the inner face of the first hollow body and a second surface facing the slot of the inner face of the second hollow body, and having a first fluid transfer aperture passing through the first surface, and a second fluid transfer aperture passing through the first surface and the second surface; the fluid transfer member having a first open end and a second closed end, wherein the first open end is in fluid communication with the first fluid transfer aperture, without fluid communication with the second fluid transfer aperture, providing a first fluid flow path through the first open end and the first fluid transfer aperture when the fluid transfer member is in the first fluid transfer position; and providing a second fluid flow path through the aperture of the first hollow connector body, the second fluid transfer aperture of the fluid transfer member, and the aperture of the second hollow connector body when the fluid transfer member is in the second fluid transfer position;
   in contact with:
   (B) a second connector comprising (a') a first hollow connector body having an inner face including a slot, and an outer face, the first hollow connector body having an aperture passing through the inner face and the outer face; (b') a second hollow connector body having an inner face including a slot, and an outer face, the second hollow connector body having an aperture passing through the inner face and the outer face; and, (c') a fluid transfer member, interposed between the first hollow connector body and the second hollow connector body, wherein the fluid transfer member is slidably arranged in the slot of the inner face of the first hollow body and the slot of the inner face of the second hollow body to provide slidable movement between a first fluid transfer position and a second fluid transfer position, the fluid transfer member having a first surface facing the slot of the inner face of the first hollow body and a second surface facing the slot of the inner face of the second hollow body, and having a first fluid transfer aperture passing through the first surface, and a second fluid transfer aperture passing through the first surface and the second surface; the fluid transfer member having a first open end and a second closed end, wherein the first open end is in fluid communication with the first fluid transfer aperture, without fluid communication with the second fluid transfer aperture, providing a first fluid flow path through the first open end and the first fluid transfer aperture when the fluid transfer member is in the first fluid transfer position; and providing a second fluid flow path through the aperture of the first hollow connector body, the second fluid transfer aperture of the fluid transfer member, and the aperture of the second hollow connector body when the fluid transfer member is in the second fluid transfer position,
   the method further comprising
   contacting the outer face of the first hollow connector body of the second connector with the outer face of the second hollow connector body of the first connector to provide a first contacting position, twisting the first hollow connector body of the second connector and/or the of the second hollow connector body of the first connector to provide a second contacting position to provide an activating position, sliding the fluid transfer member in the first connector to the second fluid transfer position while the fluid transfer member in the second connector is in the first fluid transfer position.

8. The method of claim 7 further comprising passing fluid along the second fluid flow path through the first connector and through the first fluid flow path of the second connector.

* * * * *